(12) United States Patent
Lohier et al.

(10) Patent No.: US 11,064,865 B2
(45) Date of Patent: Jul. 20, 2021

(54) ENDOSCOPE APPARATUS WITH FORCED DISPOSABILITY

(71) Applicant: REED CAM, INC., Castro Valley, CA (US)

(72) Inventors: Frantz Roger Lohier, El Cerrito, CA (US); Ali Alex Moayer, Castro Valley, CA (US)

(73) Assignee: REED CAM, INC., Castro Valley, CA (US)

( * ) Notice: Subject to any disclaimer, the term of this patent is extended or adjusted under 35 U.S.C. 154(b) by 631 days.

(21) Appl. No.: 15/901,907

(22) Filed: Feb. 22, 2018

(65) Prior Publication Data

US 2018/0263464 A1 Sep. 20, 2018

Related U.S. Application Data

(60) Provisional application No. 62/473,331, filed on Mar. 18, 2017.

(51) Int. Cl.
| | |
|---|---|
| *A61B 1/00* | (2006.01) |
| *A61B 90/98* | (2016.01) |
| *A61B 90/96* | (2016.01) |
| *A61B 90/00* | (2016.01) |

(52) U.S. Cl.
CPC ........ *A61B 1/00062* (2013.01); *A61B 1/0002* (2013.01); *A61B 1/00009* (2013.01); *A61B 1/00016* (2013.01); *A61B 1/00057* (2013.01); *A61B 1/00059* (2013.01); *A61B 1/00103* (2013.01); *A61B 1/00105* (2013.01); *A61B 1/00124* (2013.01); *A61B 1/00144* (2013.01); *A61B 90/96* (2016.02); *A61B 90/98* (2016.02); *A61B 2090/0803* (2016.02); *A61B 2090/0814* (2016.02)

(58) Field of Classification Search
CPC ............ A61B 1/00062; A61B 1/00105; A61B 1/00057; A61B 1/00103; A61B 2090/0814
See application file for complete search history.

(56) References Cited

U.S. PATENT DOCUMENTS

| | | | |
|---|---|---|---|
| 6,549,794 B1 * | 4/2003 | Nadeau, Jr. ........ | A61B 1/00142 359/511 |
| 8,460,182 B2 | 6/2013 | Ouyang | |
| 2003/0231990 A1 * | 12/2003 | Fanes, Jr. ............... | A61B 46/00 422/119 |

(Continued)

FOREIGN PATENT DOCUMENTS

| | | |
|---|---|---|
| CN | 102245076 A | 11/2011 |
| WO | 2007/047404 A2 | 4/2007 |
| WO | 2010/066787 A1 | 6/2010 |

*Primary Examiner* — Aaron B Fairchild
(74) *Attorney, Agent, or Firm* — Winston Hsu

(57) ABSTRACT

An endoscope apparatus provided in the invention has forced disposability of a cannula by the means and techniques put in place so that the parts in contact with organic tissues or the detection of container extraction cannot be used, re-used, or if re-used, in a way that aligns with their operating limits. Activation of the cannula is detected and traced using sensors or wireless intercommunication devices so that when a certain time lapses or a certain number of activations after the first activation of the cannula, a limited usage means disables the cannula in mechanical or electrical way to ensure forced disposability of the cannula.

14 Claims, 4 Drawing Sheets

(56) References Cited

U.S. PATENT DOCUMENTS

| | | | |
|---|---|---|---|
| 2007/0083111 A1* | 4/2007 | Hossack | A61B 8/4472 600/437 |
| 2007/0085686 A1 | 4/2007 | Oz | |
| 2011/0270179 A1 | 11/2011 | Ouyang | |
| 2013/0304061 A1 | 11/2013 | Chang | |
| 2014/0031629 A1 | 1/2014 | Kamimura | |

* cited by examiner

ENDOSCOPE APPARATUS WITH FORCED DISPOSABILITY

CROSS REFERENCE TO RELATED APPLICATIONS

This application claims the benefit of U.S. Provisional Application No. 62/473,331, which was filed on Mar. 18, 2017, and is incorporated herein by reference.

BACKGROUND OF THE INVENTION

1. Field of the Invention

The invention relates to a medical apparatus, and more particularly, to an endoscope apparatus with forced disposability and guaranteed with compliance of use.

2. Description of the Prior Art

Disposable endoscopes represent a new generation of cost-efficient medical instruments able to provide imagery for internal organs or obtaining biopsy samples. These instruments typically include an imaging front-end in the form of a detachable cannula incorporating various sensors, a reusable handle that connects to the cannula, and a display subsystem offering image preview, information recording or general means to configure or operate a disposable endoscope.

Today, the main purpose of disposable endoscopes is to reduce cost and increase patient safety by limiting the use of endoscope parts that may be exposed to organic tissues. This notably simplifies sterilization and reduces contagion risks. Yet, limited mechanisms exist to ensure proper operation of such instruments.

SUMMARY OF THE INVENTION

It is therefore an objective to provide a medical apparatus with a disposable part that can be forced to dispose after its first use or within a limited time(s) of use or such disposable part is compliantly used for the proper medical act.

According to an embodiment of the invention, an endoscope apparatus with forced disposability is provided, where the endoscope apparatus is restricted to a limited-time use for a cannula that is planned to be in contact with organic tissues or extracted from a sealed container. The endoscope apparatus includes a handle device having a handle and a cannula, and a limited usage means for the cannula and the handle. The limited usage means includes a detection unit and a disablement means. The detection unit is disposed at the cannula or the handle and utilized for detecting activation of the cannula. The disablement means acts as at least one of the following: a mechanical means, an electrical means, and a software means, and is utilized for disabling the cannula when a predetermined condition is met after the detection unit detecting a first activation of the cannula.

According to an embodiment of the invention, the first activation of the cannula is detected when the cannula is extracted from a container. The limited usage means further includes at least one of the following for generating a sensory result: a pressure sensor, an oxygen sensor, a thermometer, a UV or light sensor, an RFID transceiver, and an RFC antenna. When the cannula is extracted from the container, the detection unit detects activation of the cannula according to the sensory result.

According to an embodiment of the invention, the first activation of the cannula is detected when the cannula is extracted from a packaging bag having dedicated tag. The limited usage means further includes at least one of the following for generating a sensory result: a printed bar code on the packaging bag and RFID embedded in the packaging bag when the cannula is extracted from the packaging bag, the detection unit detects activation of the cannula according to the sensory result.

According to an embodiment of the invention, the handle includes a first connector and the cannula includes a second connector detachably connected to the first connector such that the cannula is detachably mounted to the handle. The first activation of the cannula is detected when the cannula is mounted to the handle for the first time.

According to an embodiment of the invention, the first activation of the cannula is detected when the cannula is in contact with organic tissues for the first time. The limited usage means further includes at least one of the following for generating a sensory result: a PH sensor, a humidity sensor, a thermometer, and a UV or light sensor. When the cannula is in contact with organic tissues, the detection unit detects activation of the cannula according to the sensory result.

According to an embodiment of the invention, the cannula includes a one-time programmable protected memory, the one-time programmable protected memory is programmed when the first activation of the cannula is detected by the detection unit.

According to an embodiment of the invention, the one-time programmable protected memory is programmed to store at least one of the following: cannula activation counter, cannula serial numbers, handle activation counter, handle serial numbers used for activation, time of the first activation, time of last cannula activation, time of last handle activation, and type of activation.

According to an embodiment of the invention, the disablement means disables the cannula a predetermined time passes or a predetermined count of activations is detected after the detection unit detecting the first activation of the cannula.

According to an embodiment of the invention, the disablement means is a processor built within the cannula or the handle. The disablement means prevents the cannula from sending any images to the handle when the predetermined condition is met after the detection unit detecting the first activation of the cannula.

According to an embodiment of the invention, a signal and power channel of the cannula to the handle is established when the cannula is mounted to the handle, and an electrical signal is conveyed through the signal and power channel to disable the cannula when the predetermined condition is met after the detection unit detecting the first activation of the cannula.

According to an embodiment of the invention, the electrical signal is provided to the handle or a display unit in the form of audio, visual, or haptic indicator.

According to an embodiment of the invention, the electrical signal is an electric current transmitted to the cannula to disable the cannula by electrically destroying the cannula.

According to an embodiment of the invention, the limited usage means further includes a latch with a shutter pin disposed adjacent to a path along which the first connector is connected to the second connector, and the shutter pin is operated by the disablement means to locate at the path when the predetermined condition is met after the detection unit detecting the first activation of the cannula.

According to an embodiment of the invention, the limited usage means further includes at least one of the following for generating a sensory result: an RFID transceiver, an NFC transceiver, and an RFC antenna. The second connector is blocked from the first connector according to the sensory result when the predetermined condition is met after the detection unit detecting the first activation of the cannula.

According to an embodiment of the invention, the cannula is integrated into the handle or embedded in the handle.

According to an embodiment of the invention, the handle includes a first connector and the cannula includes a second connector in compliance with the first connector such that the cannula is detachably mounted to the handle. The first connector comes with a predetermined electrical pin obstructed to prevent the pairing of a second connector not in compliance with the first connector.

According to an embodiment of the invention, the first connector is a female mini DIN connector or a female USB connector and the second connector is a corresponding male mini DIN connector or corresponding male USB connector.

According to the embodiments of the invention, "safe-" or "compliant-" use of such endoscope apparatus by the means and techniques put in place can be ensured that the parts in contact with organic tissues cannot be re-used or if re-used, in a way that aligns with their operating limits. Also, in the context of multi-purpose endoscopes within the scope of the invention, a need to ensure that one or more parts of an endoscope system comply with the needs of a given medical act is satisfied.

These and other objectives of the present invention will no doubt become obvious to those of ordinary skill in the art after reading the following detailed description of the preferred embodiment that is illustrated in the various figures and drawings.

DETAILED DESCRIPTION

Certain terms are used throughout the following description and claims to refer to particular system components. As one skilled in the art will appreciate, manufacturers may refer to a component by different names. In the following discussion and in the claims, the terms "include" and "comprise" are used in an open-ended fashion. Also, the term "couple" is intended to mean either an indirect or direct electrical/mechanical connection. Thus, if a first device is coupled to a second device, that connection may be through a direct electrical/mechanical connection, or through an indirect electrical/mechanical connection via other devices and connections.

A detailed description of examples of preferred embodiments is provided below. While several embodiments are described, it should be understood that the new subject matter described in the present specification is not limited to any one embodiment or combination of embodiments described herein, but instead encompasses numerous alternatives.

Disposable endoscopes offer numerous benefits over traditional reusable endoscope equipment including and not limited to cost, ease-of-use, size, patient comfort-level and simplified sterilization process. Ensuring the safe and compliant use of this new generation of devices is however largely dependent on ensuring that the disposable parts of such apparatus is used within its operating limits which includes: confirming adequacy of certain detachable parts of the apparatus towards a given medical act, limiting or suppressing reuse for certain critical part of disposable endoscope apparatus, and ensuring that sterilized packaging is traceable as part of the distribution chain of disposable endoscope parts.

Figure 1:
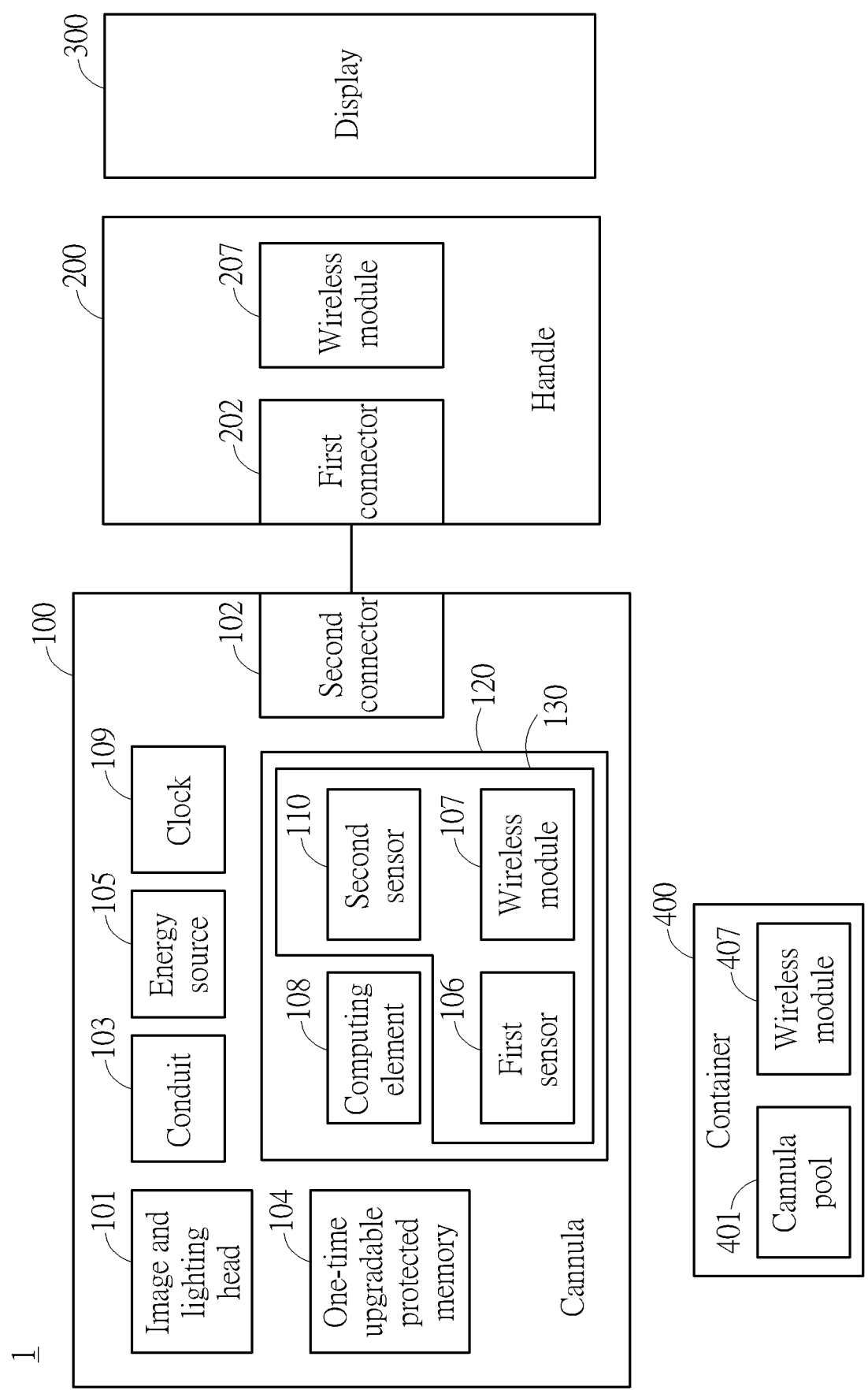
FIG. 1 illustrates a functional block diagram of an endoscope apparatus with forced disposability according to an embodiment of the invention.

Please refer to FIG. 1. FIG. 1 illustrates a functional block diagram of an endoscope apparatus with forced disposability according to an embodiment of the invention. The endoscope apparatus 1 includes a handle 200, a cannula 100 detachably mounted to the handle 200, and in some embodiments may also include a display 300 and a container 400, which has a cannula pool 401 for storage of additional disposable cannulas 100. It should be noted that the system in FIG. 1 and description follow-up is one embodiment of the invention that contains at least three separate subsystems: the cannula 100, the handle 200, and the display 300. In another embodiment of the invention, the cannula and the handle can be implemented as one subsystem, or a handle device, where the cannula is integrated into the handle or embedded in the handle and every discussion about disposability relates to the handle/cannula subsystem as a whole.

The cannula 100 may come in multiple configurations (for example with biopsy channels or not) or with different imaging and sensor capabilities. The cannula 100 conforms to a specific medical act in terms of alignment of capabilities for a given medical act aligning the characteristic of a given handle 200 or display 300 so that compliance of use of a cannula is guaranteed. The endoscope apparatus 1 is also restricted to a limited-time use for a part (the cannula 100) that is planned to be in contact with organic tissues or extracted from a container. In one embodiment of the invention, the cannula 100 may include at least some of the following components (or all of them), depending on the functionality and types of forced disposability the cannula 100 is designed to provide: an image and lighting head 101, a second connector 102, a conduit 103, a one-time programmable protected memory 104, an energy source 105, a first sensor 106, a wireless module 107, a processor 108, a clock 109, and a second sensor 110.

The handle 200 in the embodiment may include at least a first connector 202 and a wireless module 207. In one embodiment of the invention, the cannula 100 advertises its capability in an electronic fashion via the connector 102 by the processor 108 and the handle 200 then signals adequacy or non-adequacy of the cannula 100 for a given medical act to be performed using its own signaling component or the display 300 may be used to signal such match or non-match. The cannula 100 can optionally integrate the image and lighting head 101 as required. In one embodiment, the image and lighting head 101 offers local storage for images or sequence of images captured once the cannula 100 is connected to the handle 200 automatically or upon explicit activation. In another embodiment, the cannula 100 may integrate the conduit 103 allowing insertion of additional instruments or fluid canals for injecting or vacuuming liquid or gas as part of a medical procedure.

The cannula 100 can be detachably mounted to the handle 200 by detachably connecting the second connector 102 to the first connector 202 of the handle 200. In one embodiment, a signal and power channel C between the cannula 100 and the handle 200 is established when the cannula 100 is mounted to the handle 200, and electrical signals and power may be conveyed through the signal and power channel C to the cannula 100 and also to the image and lighting head 101 of the cannula 100. In one embodiment of the invention, the connector 202 receptacle of the handle 200 is designed to only accept a subset of corresponding connection from the cannula 100 for compliance of use of the cannula 100. In one configuration, the connector 202 receptacle is a female mini DIN connector and the connector 102 receptacle is a male mini DIN connector. The female mini DIN connector as the connector 202 receptacle may come with certain electrical pin(s) obstructed to prevent the pairing of a male mini DIN connector embedded in the cannula that does not conform to its intended medical act. In another embodiment of the invention, a USB connector can be used.

The image and lighting head 101 or the processor 108 is paired with the one-time programmable protected memory 104 and is able to modified the content of this memory 104 upon electric current being received from handle 200 or an explicit signal is received via the second connector 102. An electronic flash memory of OTP type (One-Time-Programmable) may be used for the one-time programmable protected memory 104. In another embodiment of the invention, the cannula 100 may hold its own energy source 105 and be able to modify the content of the one time upgradable protected memory one-time programmable protected memory 104 without any external power source.

The display 300 allows the handle 200 to transmit image coming from the cannula 100 for preview or recording, including the logging of other types of data coming from the cannula 100. The display 300 may or may not be attached to the handle 200.

To ensure the part of the endoscope apparatus 1 that is in direct contact with organic tissues can be limited to one time use or limited time(s) use, a limited usage means is provided and incorporated in the handle 200 and each cannula 100.

In the embodiment of the invention, the limited usage means includes several cooperative components in both the cannula 100 and the handle 200, and in cooperation with the display 300 and the container 400 as well. For the embodiment depicted in FIG. 1, the limited usage means 120 includes a detection unit and a disablement means. The detection unit detects and keeps track of the initial activation/use or follow-up usage of any cannula 100. The disablement means acts as a mechanical, electrical, or software means according to what the detection unit provides to force a cannula 100 into unavailable status, i.e., forced disposability.

There are several ways in determining when a cannula 100 is initially activated, or when a first activation of the cannula 100 can be detected. For example, the first activation of a cannula 100 occurs when the cannula 100 is extracted from a sealed container, or the cannula pool 401 of the container 400 in one embodiment as illustrated in FIG. 1. For a cannula packaged with dedicated packaging bag, which may include unique printed bar code on the surface or RFID tag embedded, the first activation of such cannula 100 occurs when the cannula 100 is removed from the dedicated packaging bag (RFID sensed by the cannula 100) or the bar code is scanned before the cannula 100 is removed. The first activation of a cannula 100 may also occur when the cannula 100 is detected via electric powering with the handle 200, which means when the cannula 100 is mounted to the handle 200 for the first time. The first activation of a cannula 100 may also occur as defined by the cannula 100 being in contact with organic tissues for the first time.

Figure 2:
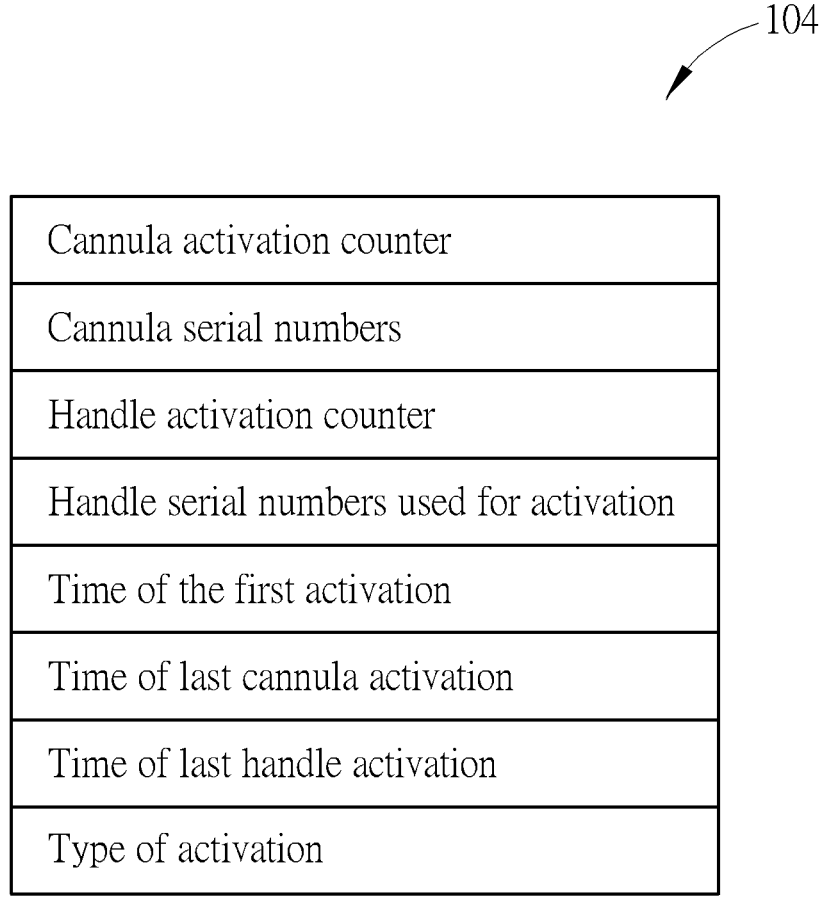
FIG. 2 is a schematic diagram showing the content of the one-time programmable protected memory store.

Please refer to FIG. 2, which is a schematic diagram showing the content of the one-time programmable protected memory store. The data of activation, along with other usable information of the cannula 100, is stored in the one-time programmable protected memory 104 and in one embodiment can be written once, or in another embodiment, all of sub segments of this one-time programmable protected memory 104 can be programmed. In one embodiment, the one-time programmable protected memory 104 contains multiple segments able to record activation information for the cannula 100, handle 200 or both devices. Segments of the one-time programmable protected memory enable to trace cannula activation counter, cannula serial numbers, handle activation counter, handle serial numbers used for activation, time of the first activation, time of last cannula activation, time of last handle activation, and type of activation (reason for activation e.g., pressure sensor, light sensor, NFC activation, electrical pairing, etc.).

The limited usage means 120 embodied in the example of FIG. 1, may include one or more of the first sensor 106, the wireless module 107, the processor 108, and the second sensor 110, according to how the first activation of the cannula 100 will be detected. The detection unit 130 may be defined to include at least one of the first sensor 106, the wireless module 107, and the second sensor 110. Regarding the case that the first activation of a cannula 100 occurs when the cannula 100 is extracted from the cannula pool 401 of the container 400, the first sensor 106 may contain at least one of a pressure sensor, an oxygen sensor, a thermometer, and a UV or light sensor, and the wireless module 107 may be an RFID transceiver and/or an RFC antenna, and when the cannula 100 is extracted from the container 400, the detection unit detects the first activation of the cannula 100, so that the one-time programmable protected memory 104 can be programmed according to the sensory result generated by the first sensor 106 or the wireless module 107. Generally, the one-time programmable protected memory 104 may be programmed by the processor 108 of the cannula 100, or by a processor on the handle 200. In another embodiment, the programming may also carried out by a processor in the display 300 remotely or through wire connected between the display 300 and the handle 200. For example, updating the one-time programmable protected memory 104 may be triggered by a pressure sensor in the cannula 100 that detects the cannula 100 is being removed from the pressurized container 400 or a compartment of the container 400. In another embodiment, the oxygen sensor, the thermometer, or the UV sensor is used to determine that a cannula 100 is voluntarily or non-voluntarily extracted from the container 400 or that the environment of the container 400 is changing. In still another embodiment, the RFID and/or RFC antenna and transceiver in the cannula 100 may be used to detect that the cannula 100 is removed from or introduced into the container 400 by mean of RF waves communicating with a wireless module 407 (RFID/NFC module) of the container 400.

It should be noted that in one embodiment of the invention, the RF circuitry of the cannula 100 can be used to program certain attributes of the cannula 100, such as the number of time(s) that the cannula 100 can be used. The RF circuitry of the cannula 100 can also be used to program the mechanical configuration of the cannula 100 including to code the presence of the conduit 103 or certain attributes of the image and lighting head 101 such as supported image resolutions. This programming can be done after the cannula 100 is sterilized and contained.

Regarding the case that the first activation of a cannula 100 occurs when the cannula 100 is mounted to the handle 200, electric signal from the handle 200 via the signal and power channel C can be detected by the processor 108 and the one-time programmable protected memory 104 is then programmed accordingly.

Regarding the case that the first activation of a cannula 100 occurs when the cannula 100 is having contact with organic tissues for the first time, the second sensor 110 may contain at least of a PH sensor, a humidity sensor, a thermometer, or a light or UV detection sensor. The second sensor 110 may be used to detect the introduction of the cannula 100 as means to determine contact with organic tissues and the sensory result triggers the first activation of the cannula 100. For example, using the light or UV detection sensor to sense the light transition (ambient light or from the image and light head 101) from light to dark and to light again when the cannula 100 is inserted into the organic tissue helps determining that the cannula 100 is having contact with the organic tissues.

Once the first activation of the cannula 100 is detected and the one-time programmable protected memory 104 is then programmed by the processor 108 with a new set of information reflecting an activation count. In one embodiment, a timestamp corresponding to the activation time of the cannula 100 using the clock 109 is part of the information set stored in memory 104.

The disablement means, or the processor 108 in this embodiment, acts as an electrical or software means to disable the cannula 100 when a predetermined condition is met, such as a certain time after the first activation or some more activations after the first activation of the cannula 100. For example, upon subsequent initial use of a limited-use cannula 100, or detection of extraction of the cannula 100 from sealed storage of the container 400, or detection that a maximum activation was achieved or that a certain amount of time has lapsed since the cannula 100 was first activated or extracted from concealment, the processor 108 may limit the use of the cannula 100, whether it was made in touch with human tissues or not.

In one embodiment, the cannula 100 is disabled by the processor 108 preventing the image and lighting head 101 from sending any images or sequence of images to the handle 200 via connector 102.

In another embodiment, warning signals are used. The handle 200 may receive information that the cannula 100 was previously used by electronic mean and information about the date/time of use or de-concealment of the cannula 100 from the processor 108 of the cannula 100. In another embodiment of the invention, such contextual information may be signaled to the display 300 in the form of audio, visual, or haptic indicator. In another embodiment of the invention, similar notification mechanisms may be directly integrated within the handle 200 or the cannula 100. In addition, the container 400 may also signal that one or more cannulas 100 in the cannula pool 401 was previously used via intercommunication between the wireless module 407 incorporating an RFID/NFC antenna transceiver and the wireless module 107 of the cannulas 100.

In another embodiment, an electric current may be transmitted from the handle 200 to the cannula 100 to disable the cannula 100 once the 'used' cannula 100 that should be disabled is mounted to the handle 200. The electric current electrically destroys the cannula 100 by burning the fuse, if any, of the cannula 100 or any critical components within the cannula 100.

Figure 3:
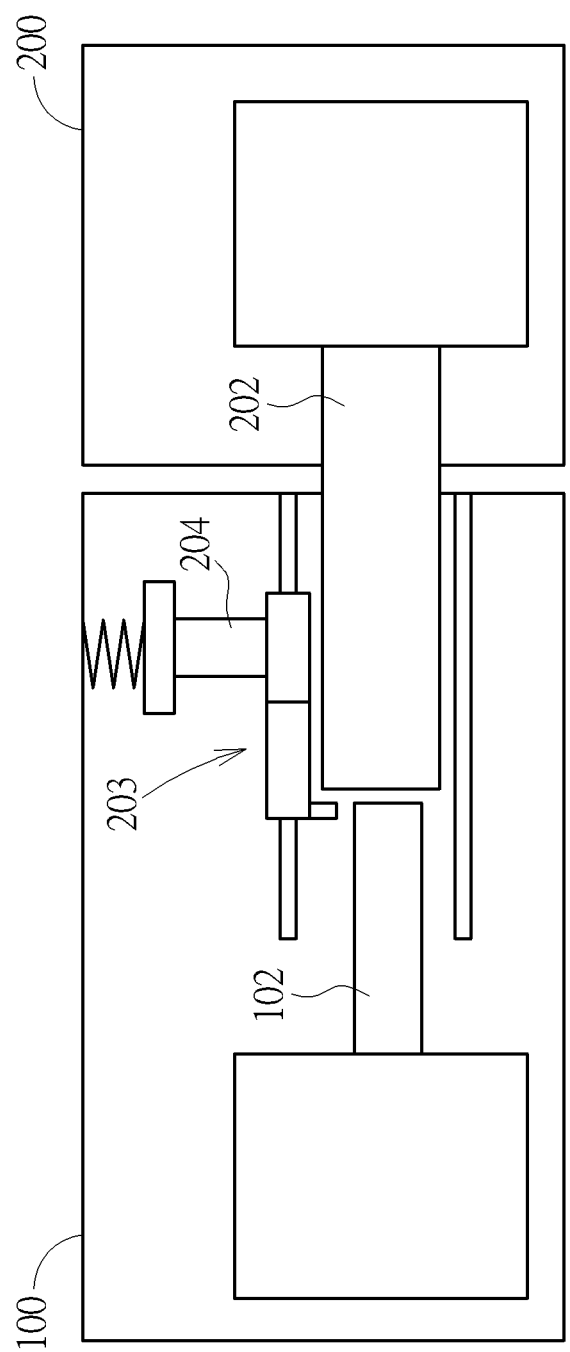
FIG. 3 is a schematic diagram of the cannula mounted to the handle using a latch operated by the disablement means.
Figure 4:
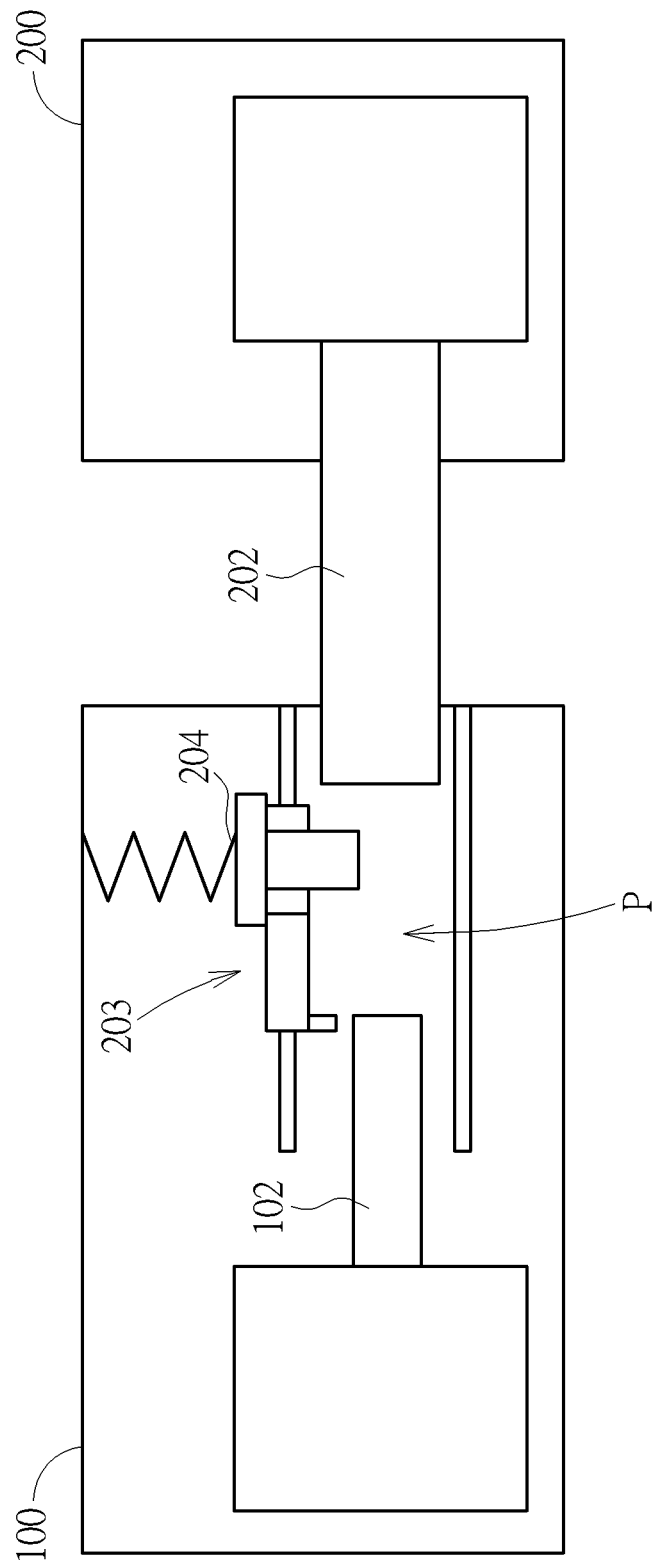
FIG. 4 is a schematic diagram of the cannula being disabled by the latch.

In another embodiment, the connection between the 'used' cannula and the handle is blocked, either mechanically or electrically, so that a 'used' cannula will not be able to be mounted to the handle. Please refer to FIG. 3 and FIG. 4. FIG. 3 is a schematic diagram of the cannula mounted to the handle using a latch operated by the disablement means and FIG. 4 is a schematic diagram of the cannula being disabled by the latch. In the embodiment, the limit usage means includes a latch 203 with a shutter pin 204 disposed adjacent to a path P along which the first connector 202 is connected to the second connector 102. For the first time or not going beyond the limit the cannula 100 can be used, the shutter pin 204 is retracted away from the path P, controlled by the handle 200 or the processor 108, as depicted in FIG. 3. When the cannula 100 is no longer usable, the shutter pin 204 is then operated by the disablement means, the handle 200 or the processor 108, to locate at the path P so as to mechanically obstruct the receiving part of the second connector 108 to prevent subsequent attachment between the cannula 100 and the handle 200. The mechanical latch 203 is used to block exposure of certain electrical signal or the pairing of electrical pins between the cannula 100 and the handle 200.

In another embodiment, blockage of certain electro-mechanical contacts from the second connector 102 may be triggered via the proximity detection of the cannula 100 using an RFID transceiver, an NFC transceiver, or an RFC antenna. Other Radio Frequencies (RF) may be employed in other embodiments of the invention.

In still another embodiment, electrically triggered magnets may also be used between the cannula 100 and the handle 200 to shutter-off or repulse electronic or mechanical connections.

The endoscope apparatus provided in the invention has forced disposability of a used cannula by the means and techniques put in place so that the parts in contact with organic tissues or extracted from concealed containers cannot be re-used or if re-used, in a way that aligns with their operating limits. Activation of the cannula is detected and traced using sensors or wireless intercommunication devices so that when a certain time lapses or a certain number of activations after the first activation of the cannula, a limited usage means disables the cannula in mechanical or electrical way to ensure forced disposability of the cannula.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. An endoscope apparatus with forced disposability, where the endoscope apparatus is restricted to a limited-time use for a cannula that is planned to be in contact with organic tissues or extracted from a sealed container, the endoscope apparatus comprising:
   a handle device comprising a handle and the cannula; and
   a limited usage means for the cannula and the handle, comprising:
      a detection unit comprising at least one sensor disposed at the cannula or the handle for detecting activation of the cannula; and
      a disablement means acting as an electrical means for disabling the cannula when a predetermined condition is met after the detection unit detecting a first activation of the cannula, wherein a signal and power channel of the cannula to the handle is established, an electrical signal is conveyed through the signal and power channel to disable the cannula when the predetermined condition is met after the detection unit detecting the first activation of the cannula, and the electrical signal is an electric current transmitted to the cannula to disable the cannula by electrically destroying the cannula.

2. The endoscope apparatus of claim 1, wherein the first activation of the cannula is detected when the cannula is extracted from a container.

3. The endoscope apparatus of claim 2, wherein the limited usage means further comprises at least one of the following for generating a sensory result: a pressure sensor, an oxygen sensor, a thermometer, a UV or light sensor, an RFID transceiver, and an RFC antenna, and when the cannula is extracted from the container, the detection unit detects activation of the cannula according to the sensory result.

4. The endoscope apparatus of claim 1, wherein the first activation of the cannula is detected when the cannula is extracted from a packaging bag having dedicated tag.

5. The endoscope apparatus of claim 4, wherein the limited usage means further comprises at least one of the following for generating a sensory result: a printed bar code on the packaging bag and RFID embedded in the packaging bag, and when the cannula is extracted from the packaging bag, the detection unit detects activation of the cannula according to the sensory result.

6. The endoscope apparatus of claim 1, wherein the handle comprises a first connector and the cannula comprises a second connector detachably connected to the first connector such that the cannula is detachably mounted to the handle, wherein the first activation of the cannula is detected when the cannula is mounted to the handle for a first time.

7. The endoscope apparatus of claim 1, wherein the first activation of the cannula is detected when the cannula is in contact with organic tissues for a first time.

8. The endoscope apparatus of claim 7, wherein the limited usage means further comprises at least one of the following for generating a sensory result: a PH sensor, a humidity sensor, a thermometer, and a UV or light sensor, and when the cannula is in contact with organic tissues, the detection unit detects activation of the cannula according to the sensory result.

9. The endoscope apparatus of claim 1, wherein the disablement means is a processor built within the cannula or the handle.

10. The endoscope apparatus of claim 9, wherein the disablement means prevents the cannula from sending any images to the handle when the predetermined condition is met after the detection unit detecting the first activation of the cannula.

11. The endoscope apparatus of claim 1, wherein the electrical signal is further provided to the handle or a display unit in the form of audio, visual, or haptic indicator.

12. The endoscope apparatus of claim 1, wherein the cannula is integrated into the handle or embedded in the handle.

13. The endoscope apparatus of claim 1, wherein the handle comprises a first connector and the cannula comprises a second connector in compliance with the first connector such that the cannula is detachably mounted to the handle, the first connector coming with a predetermined electrical pin obstructed to prevent the pairing of a second connector not in compliance with the first connector.

14. The endoscope apparatus of claim 13, wherein the first connector is a female mini DIN connector or a female USB connector and the second connector is a corresponding male mini DIN connector or corresponding male USB connector.

* * * * *